United States Patent [19]

Peck

[11] Patent Number: 4,819,645
[45] Date of Patent: Apr. 11, 1989

[54] DERMAL SUBSTANCE COLLECTION METHOD

[75] Inventor: Carl C. Peck, Rockville, Md.

[73] Assignee: The United States of America as represented by the Secretary of the Army, Washington, D.C.

[21] Appl. No.: 116,763

[22] Filed: Nov. 4, 1987

Related U.S. Application Data

[62] Division of Ser. No. 660,778, Oct. 8, 1985, Pat. No. 4,706,676.

[51] Int. Cl.$^4$ ................................................ A61B 5/00
[52] U.S. Cl. .................................... 128/632; 128/760
[58] Field of Search ............... 128/760, 767, 632, 637; 604/290

[56] References Cited

U.S. PATENT DOCUMENTS 4,329,999 5/1982 Phillips ............................... 128/760

Primary Examiner—Edward M. Coven
Assistant Examiner—Randy Citrin
Attorney, Agent, or Firm—Anthony T. Lane; William V. Adams; Werten F. W. Bellamy

[57] ABSTRACT

A dermal substance collection device (DSCD) is described which provides means for the non-invasive, instantaneous and continuous monitoring of chemical substances which are present in a detectable amount in either or both interstitial fluid or sweat or which are on or in the skin. The transdermal substance collection device of this invention is comprised of three essential components: (1) a substance binding reservoir, wettable by (2) a liquid transfer medium which allows for liquid bridge transfer of a soluble substance from the skin surface to the binding reservoir by virtue of its wettability by the liquid, and (3) an occlusive cover.

20 Claims, 4 Drawing Sheets

DERMAL SUBSTANCE COLLECTION METHOD

CROSS REFERENCE

This application is a divisional of U.S. patent application Ser. No. 660,778, filed Oct. 8, 1985, now U.S. Pat. No. 4,706,676, will issue Nov. 17, 1987.

FIELD OF THE INVENTION

This invention relates to a convenient integral or self-contained non-invasive dermal substance collection device easily reversibly attachable to a dermal surface for use in detection, routine monitoring and research in the areas of compliance With therapeutic regimens and exposure to substances of abuse or environmental toxic chemicals or xenobiotics, and investigation of endogenous substances.

BACKGROUND OF THE INVENTION

A variety of imperfect techniques are available to assess human exposure to chemicals. Detection of environmental levels of chemicals by means of, for example, air sampling devices fails to yield information on actual extent of body exposure e.g., actual entry into the body. Most known techniques for assessing the actual extent of body exposure to chemicals suffer from their invasiveness (e.g. tissue biopsies, blood sampling) or their impracticality (e.g. collection of urine or saliva). With the exception of continuous urine collections, most known systems do not provide information on cumulative exposure over a period of time.

A system which addresses the need to provide detection of a drug material with correlation with time in order to obtain useful information concerning drug absorption, excretion, metabolism rates and metabolites is described in U.S. Pat. No. 3,649,199 to D. P. Littlejohn; however, attachment of the patient to the analytical instrumental is required. This patent describes a method for detecting trace quantities of an organic drug material in a living animal which involves passing a sample of gaseous material effusing from the animal by breath, through the skin or from the blood stream through a multi-stage membrane gas separator to enrich the concentration of the organic drug material in the gaseous sample. The enriched sample gas output of the membrane separator is fed to a gas analyzer such as a mass spectrometer for detection of the organic drug material. This patent describes the obtention of a sample of gaseous material from a region immediately adjacent the skin of the animal by means of a gas impervious sleeve clamped to the forearm of a person for the containment of a carrier gas such as nitrogen or helium.

U.S. Pat. No. 3,552,929 to R. P. Fields et al. describes a device for detecting halide ion concentration in a fluid such as human perspiration for the diagnosis of cystic fibrosis. The device is used in conjunction with an absorptive sweat collection patch which is described as a piece of filter paper under a polyethylene overlayer to prevent evaporation.

U.S. Pat. No. 4,329,999 to M. Phillips is directed to a clinical test device more specifically described as a sweat collection patch for monitoring a human patient for the presence of sweat-excreted drugs such as alcohol. Other drugs such as digoxin, lithium, anti-convulsants, or morphine excreted in sweat are also disclosed as detectable by the patch but no specific details or experiments are provided. The patch device according to this patent is disclosed as inexpensive, easy to use, non-intrusive and capable of yielding accurate and precise measurements in that the patch is capable of collecting sweat in a continuous manner and at a steady rate. The circular shaped patch is described as including a backing member, a stripping member, a base, a collecting pad and a cover member having an adhesive surface contiguous to the collecting pad. This patent further discloses that the collecting pad includes a plurality of layers of polyester-type absorbent material formed by a certain method including thoroughly wetting the polyester with a saturated aqueous solution of sodium chloride and subsequently causing the precipitation of sodium chloride in the polyester material The discs formed from the dried polyester are then wetted with a solution, preferably containing Nystatin, sodium fluoride and reduced methylene blue. This patent discloses that the Nystatin is used to inhibit fungal proliferation since fungi could cause metabolic breakdown of ethanol and/or metabolic breakdown of glucose in sweat to ethanol and methanol. The sodium fluoride is described as inhibiting anaerobic glycolysis in bacteria and fungi and hence the production of ethanol. The reduced methylene blue is used as a visual indicator when the patch is removed since in a wet patch it turns bright blue in the presence of oxygen. This patent further discloses that magnesium sulfate, fructose or urea may be used in lieu of sodium chloride in that this patch element must be an osmotically active highly soluble crystalloid.

The patch according to this patent is said to yield for drug assay virtually all of the collected sweat when, presumably, the pad of the patch is spun in a specially constructed centrifuge tube. The reverse flow of sweat from the absorbent pad in the cover member chamber through the base member is described as controlled by the relative size and orientation of the base member hole and the chamber containing the pad which is said to permit sweat to easily enter the absorbent pad but inhibit the reverse flow of sweat out of the chamber.

An earlier sweat collecting device is described in M. Phillips, R. E. Vandervoort and C. E. Becker, "Long-term Sweat Collection Using Salt impregnated Pads"; *J. Invest. Dermatol.*, 68:221–224 (1977). The pad described therein was a square cut from a commercially available disposable diaper material consisting of a layer of absorbent cotton sandwiched between a sheet of waterproof polyurethane on one side and two layers of porous, woven rayon on the other. Both sodium chloride impregnated as well as control pads were prepared. The device incorporating this pad was constructed by applying to the patient an adhesive template, then placing the pad over the template, covering the pad with a square of this plastic sheet and thereafter sealing the assembled device in place on the patient with a square of waterproof adhesive tape.

The foregoing work, inter alia, is referred to in C. C. Peck, M. Phillips, C. E. Becker and K. L. Melmon "Drug Measurement in Sweat: A New Approach in Clinical Pharmacology", Abstracts, Fifth Pharmacology-Toxicology Program Symposium, National Institute of General Medical Sciences, p. 29; (1977).

The authors, noting problems created by intermittent or erratic alcohol ingestion, disclosed the undertaking of a theoretical analysis to determine technical requirements for an optimal sweat collection device which involved mathematical simulation of the dynamics of a drug in sweat assuming drug disposition with one compartment, zero or first-order excretion kinetics and first-order transfer of drug between the body and the sweat collection device. The authors disclose the conclusion that (1) sweat flow into the device must be continuous and constant, (2) drug losses from the device, both external and back-transfer into the body, must be minimized, (3) drug bound in the device must be extractable for qualitative analysis, and (4) the sweat collection device should be small (<2 cm$^2$), safe, and acceptable to the subject being studied. It is stated that development of a suitable sweat collection device may contribute particularly to the study of bioavailability, to the clinical assessment of compliance with therapeutic regimens, and to the diagnosis of addictive states such as alcoholism.

A later article by M. Phillips, "An Improved Adhesive Patch For Long-Term Collection of Sweat", *Biomat., Med. Dev., Art. Org.*, 8(1), 13–21 (1980), refers to the practical limitations of the adhesive skin patch of the above-referred to M. Phillips et al. 1977 article and describes the structure and structure and evaluation of an improved adhesive patch similar in some respects to that described in U.S. Pat. No. 4,329,999 to M. Phillips. The use of soluble crystalloid material such as sodium chloride, magnesium sulfate, urea, fructose and sucrose is disclosed. The adhesive patch device of the M. Phillips et al. 1977 article was also referred to in C. C. Peck et al., "Continuous Transepidermal Drug Collection:- Basic for Use in Assessing Drug Intake and Pharmacokinetics", *J. Pharmacokinetics and Biopharmaceutics* 9(1):41–58 (1981) which report explores a theoretical basis for the use of transepidermal drug collection in assessing various aspects of drug pharmacokinetics, with emphasis on its use in the quantitation of cumulative amount of drug exposure. The influence and implications of single and polyexponential drug disposition kinetics; zero-, first-order, and Michaelis-Menten excretion functions; and back transfer of drug from the collection device were explored.

The M. Phillips et al. 1977 article and the M. Phillips 1980 article Were also referred to in C. C. Peck et al. "Mechanism of Noninvasive Collection of Substances Dissolved in Interstitial Fluid", *Clinical Research*, Vol. 30, No. 2 (256A) April 1982. This excerpt reports test of the hypothesis that the transepidermal fluid collection method according to M. Phillips can be used to collect substances dissolved in interstitial fluid by application to rabbits, a species without sweat glands. Collection devices according to the Phillips 1980 paper were tested on the rabbits for detection of $^{22}$Na with observations leading to postulation of a mechanistic theory of transepidermal fluid collection of non-volatile substances dissolved in interstitial fluid: (1) pre-wetting the Phillips pads leads to hydration of stratum corneum, thus increasing its permeability to substances in the interstitial fluid; (2) hydrated stratum corneum acts as a semipermeable membrane separating two aqueous regions; (3) movement of substances from interstitial fluid across stratum corneum into the Phillips collection device follows thermodynamic principles. Peck et al. conclude that this theory is consistent with that postulated previously by Peck et al. (1981) and should be tested in man.

The device of the Phillips (1980) article as well as the theoretical analysis of Peck et al. (1981) was also treated in C. C. Peck et al., "A Noninvasive Transepidermal Toxicological Monitoring Device", Pittsburgh Conference and Exposition on Analytical Chemistry and Applied Spectroscopy, p. 366 Abstract, 1982. Therein is disclosed the modification of a Phillips experimental prototype transepidermal fluid collection device by the insertion of an activated charcoal cloth or a Teflon disk, on which is impregnated activated charcoal, between the pads of the collection device. The abstract discloses that incorporation of activated charcoal into the device retards back-transfer of theophylline by an average of 50% but results were variable. The abstract concludes with the statement that improvements in the adhesiveness, water-tightness and other structural features of the device are required in order to reduce the variable uptake and binding of theophylline and that reliable xenobiotic uptake and prevention of back-transfer may lead to extension of the utility of transepidermal fluid collection from qualitative to quantitative surveillance of human exposure to xenobiotics.

Other dermal patch devices are known which differ in components and which serve different purposes than the device of this invention. One is a drug delivery device comprising a drug-containing polymeric diffusion matrix which can be applied as a transdermal patch with means for fastening the matrix to the skin of a person as disclosed in U.S. Pat. No. 4,321,252. Another is what appears to be an adhesively attachable electrode for monitoring vital signs. The metal electrode projects through a molded plastic shell which contains a rather porous sponge-like packing with a liquid substance, presumably containing an electrolyte. The shell is encircled by an attached ring of a form substance having an adhesive surface for dermal attachment.

Similarly, in the context of ease of application, the discovery of the dermal substance collection device according to this invention makes available means for the convenient, non-invasive, immediate and continuous collection of a chemical substance from a body's dermal surface by simple application of the device thereto.

SUMMARY OF THE INVENTION

A dermal substance collection device (DSCD) is described, which provides means for the non-invasive, immediate and continuous monitoring of chemical substances which have either entered the body or are synthesized in the body and which are present in a detectable amount in either or both interstitial fluid or sweat or which are on or in the skin. The dermal substance collection device of this invention is comprised of three essential components: (1) a substance binding reservoir, (2) a liquid transfer medium which allows for liquid bridge transfer of a soluble substance from the skin surface to the binding reservoir by virtue of its wettability by the liquid, and (3) an occlusive cover.

An embodiment of this invention concerns a flexible and adhesive cover having a cavity completely occupied by the liquid transfer medium and substance binding reservoir and which occlusively maintains the liquid transfer medium in contact with a dermal surface to which the device is applied. Another embodiment relates to a dermal substance collection device comprising an immobilized collection composition composed of an immobilized liquid transfer medium and a substance binding reservoir, maintained in contact with a dermal surface by an occlusive cover. The collection composition can be gelled and the occlusive cover can then be limited to a metallic foil having an adhesive surface or it can additionally comprise an overlaying layer of flexible waterproof adhesive tape. A further embodiment of this invention found to be particularly suitable for monitoring a water soluble chemical utilizes an aqueous salt solution immobilized by agarose as a gel matrix liquid transfer medium, activated charcoal powder as the substance binding reservoir dispersed and immobilized in the gel matrix wherein the gel matrix transfer medium is contained in a cavity defined by a surrounding occlusive flexible covering comprised of closed cell foam, metallic foil, and an overlayer of waterproof plastic adhesive tape so that an exposed protruding portion of the gel matrix composition, relative to the device-dermal surface interface, is capable of maintaining positive pressure contact with the dermal surface to which the device is adhesively applied. The device according to this invention provides immediate and continuous juxtaposition of the transfer medium with the surface of the skin enabling movement of the target chemical by a liquid bridge from the body into contact with the binding reservoir in order to provide for early accumulation and minimize back transfer of the chemical. A method for the non-invasive, immediate and continuous monitoring of a human or lower animal chemical substance, either endogenous or by virtue of exposure to these substances, comprising use of the subject device and analysis for the chemical substance collected is also described. More precisely, this invention relates to a composition of matter and the use thereof in a method for the non-invasive, immediate and continuous collection of a chemical substance from a dermal surface. The method comprises applying to the dermal surface a dermal substance collection device which is comprised of (a) a binding reservoir material for binding with said dermal substance to prevent back transfer loss of said dermal substance from said collection device to the dermal surface; (b) a liquid bridge transfer medium which allows the instantaneous and continuous transfer of said dermal substance from the dermal surface to said binding reservoir material, said binding reservoir material being maintained in a wet-state by said liquid transfer medium; and (c) a cover means for occlusively containing said binding reservoir material and said liquid bridge transfer medium and for occlusively maintaining said liquid bridge transfer medium in continuous contact with the dermal surface upon application of said collection device to the dermal surface. The dermal collection device is preferably circular in shape. Moreover, it has a flat profile relative to the dermal surface upon adhesive, an immobilized liquid transfer medium, approximately 1 millimeter to 7 centimeters in diameter and 1 millimeter to 0.5 centimeters in thickness and a strippable backing. The liquid transfer medium is immobilized and contains binding reservoir material dispersed therein. This binding reservoir material is selected from the group consisting of activated charcoal, ion exchange resin, immobilized antibody, silica, zeolite and molecular sieve and the immobilized liquid bridge transfer medium is an aqueous gel. The gel may contain osmotically active substance such as, a penetration enhancing agent, which includes n,n-di-ethyl-m-toluamide, 1-dodecylazacyclo-heptan-2-one, and dimethylsulfoxide or a gelling agent. The gelling agent is preferably agarose or polyvinyl alcohol polymer, or a combination thereof. The osmotically active aqueous solution may contain sodium chloride in an amount up to the saturation level of the aqueous gel. In such a solution, the amount of agarose can be 0.5 to 30 percent by weight of the aqueous sodium chloride solution preferably about 3 percent, and the amount of activated charcoal can be 0.5 to 30% by weight of the aqueous gel, preferably, about 5 percent. The occlusive cover means is comprised of an outer adhesive layer and an inner metallic foil layer contiguous to the immobilized liquid bridge transfer medium. Additionally, the occlusive cover means may comprise a transfer medium-surrounding closed-cell foam layer contiguous to the foil layer. The immobilized liquid bridge transfer medium comprises a protruding surface relative to the occlusive cover means and the dermal surface-interface to maintain positive pressure contact between the transfer medium and the dermal surface.

DETAILED DESCRIPTION OF THE INVENTION

Figure 2:
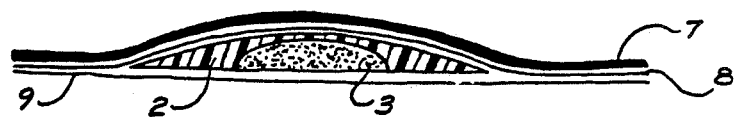
FIG. 2 is a side view of a device according to the present invention in storage form.

A dermal substance collection device 1 (DSCD) according to this invention broadly can be described as comprised of three essential components: (1) a substance binding reservoir wettable by (2) a liquid transfer medium, and (3) an occlusive cover. The DSCD of FIG. 2 describes internally, a composition 3 containing a substance binding reservoir and a liquid transfer medium, the composition 3 contained in a cavity defined by occlusive cover 2 which can be a smooth, transparent or opaque plastic such as a polyolefin. The device can have a strippable layer 9 for storage and the occlusive cover can comprise a waterproof flexible overlayer 7 with adhesive layer 8 or can alternatively be fixed to the dermal surface with other fastening means such as a VELCRO or elastic band.

Figure 3:
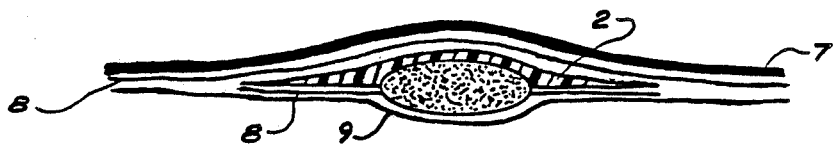
FIG. 3 is a side view of a device according to the present invention showing a preferred construction.

A DSCD device having a preferred feature is described in FIG. 3 wherein is shown a substance collection composition 3 having an immobilized shape, for example, a gel surrounded by an occlusive adhesive cover of components 2 and 7. In this instance, the substance collection composition is self-supporting and component 2 may not be necessary, an occlusive layer 7 of adhesive foil and/or flexible waterproof adhesive tape being satisfactory to maintain contiguity between the device's collection composition and the dermal surface to which it is applicable. Upon application to a dermal surface after stripping of protection layer 9, the gelled composition's protruding shape facilitates maintenance of a positive pressure contact with the dermal surface. This protruding portion of the composition can be facilitated by provision of the composition as variously a gel, thixotropic mixture, paste or semi-solid depending upon the components and their physical or chemical state as related to the desired target chemical. The immobilizing agents are, of course, compatible for contact with the skin. Immobilization of the liquid transfer medium by formation of a gel from addition of a polymeric gelling agent has been found particularly suitable for the experimental procedures utilized in development of this invention and described below in detail.

Figure 1:
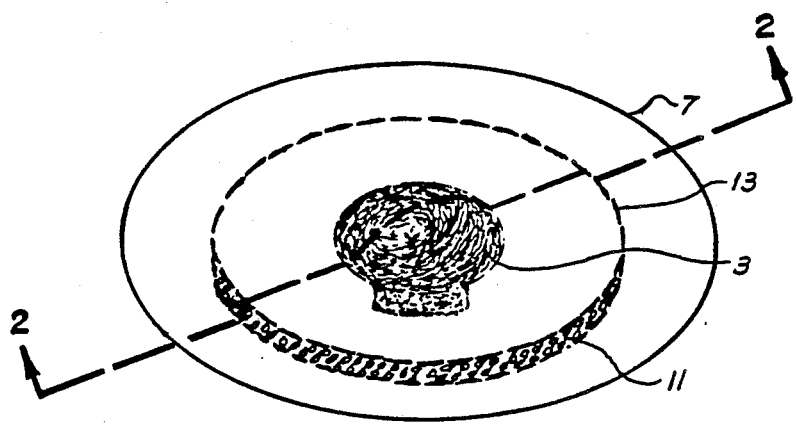
FIG. 1 is a perspective of a transdermal substance collection device applied to a dermal surface according to this information.
Figure 4:
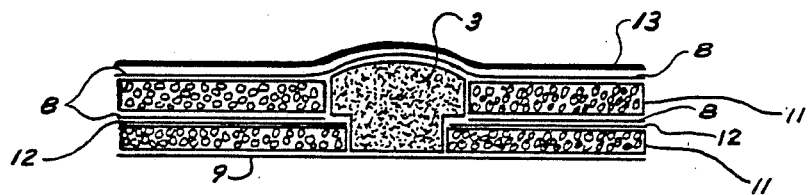
FIG. 4 is a side view of a device in storage form according to the present invention showing the best mode.
Figure 5:
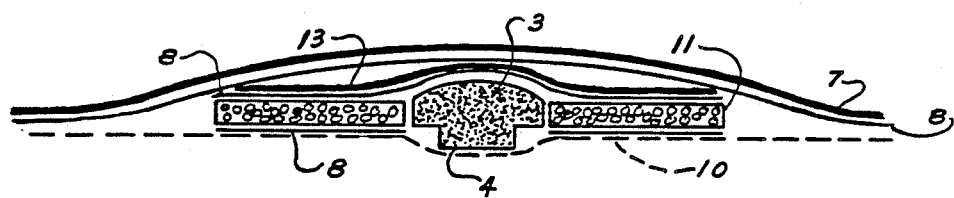
FIG. 5 is a side view taken along line 2—2 of FIG. 1 showing the device of FIG. 4 as applied to the dermal surface in FIG. 1.

FIG. 4 describes a preferred device in storage form, where the device contains an immobilized collection composition having a gel matrix. FIG. 5 shows this device as applied to a dermal surface 10 as shown in FIG. 1. This device as constructed according to the procedure later described contains an immobilized composition 3 containing a substance binding reservoir and a liquid transfer medium so that the bottom stem portion 4 insures contact with a dermal surface. Laminate components 11 are advantageously an occlusive closed cell polyurethane foam, layer 12 is a wax-paper protective and advantageous separative layer which originally is formed as a component of a commercial tape of the polyurethane foam. Laminate component 13 is advantageously an occlusive metallic foil such as an impermeable aluminum foil. The preferred DSCD is constructed so that upon application, the immobilized liquid transfer medium is juxtaposed directly to skin, enabling the continuous migration of a substance from the body across the skin into the liquid medium and binding reservoir. After wearing the DSCD for a period of time (hours to days), the DSCD is removed from analysis. Analysis consists of chemically separating the bound substance of interest from the binding reservoir for qualitative and quantitative measurement by conventional techniques. The measured amount of collected substance is related to cumulative body exposure of the substance using known data analytic techniques such as described in the C. C. Peck et al. (1981) paper (supra).

The term immediate as used to describe the action of the collection device according to this invention, in contradistinction to the delayed onset of collection of the Phillips device referred to previously, refers to both time and space conditions necessary for passive transfer of a chemical substance from the skin, interstitial fluid or sweat into the device which are established without delay upon emplacement of the device on the dermal surface by virtue of the insured contact which the liquid bridge provides to the stratum corneum of the dermal surface which hydrates thereby creating the permeable membrane in contact with both fluid spaces.

The device of this invention provides for reproducible results. In order to obtain this reproducibility, the surface area of adherence of the composition such as a gel medium to the skin should be fixed insofar as feasible and the composition in contact with the dermal surface rendered stationary. This is facilitated by use of a binding means such as a surrounding adhesive bordering the composition which maintains the location of the composition vis-a-vis the dermal surface and facilitates reproducibility of results.

A Phillips device obtained from 3M Company as referred to previously has an important limitation in that the transparent plastic used to construct the right-angular raised cylindrical container and surrounding rim is very rigid compared to the encircling area of translucent flexible adhesive so that the device as a whole is relatively non-flexible in comparison to the flexible and relatively flat-profiled device of comparable diameter according to this invention. This limitation promotes deleterious leakage or unintended abrasive removal of the Phillips device from the skin of a person by virtue of its raised profile and bulk.

An embodiment of this invention particularly suitable for monitoring water soluble substance utilizes an aqueous sodium chloride solution immobilized by agarose as a gel matrix transfer medium, activated charcoal powder dispersed and immobilized in the gel matrix as a binding reservoir, and an occlusive flexible adhesive cover comprising an overlayer of a water-proof plastic adhesive tape. For example 3 gm agarose+5 gm activated charcoal powder are mixed with 100 cc 30% saline (30 gm NaCl in 100 gm distilled water) at a temperature of about 100° C. When the agarose is completely dissolved and the charcoal is uniformly dispersed in the solution, the mixture is poured into a 2 mm×1.5 ca diameter circular mold made in adhesive closed cell foam polyethylene tape. In order to insure that the DSCD will enable constant pressure contact of the transfer medium against skin, the mold is constructed so that a 0.5 mm diameter circular stub of agarose gel will protrude 2 mm beyond the level of the inner surface of the adhesive closed cell foam polyurethane tape. Cooling to room temperature (25° C.) results in gelling of the mixture. The external side is covered with a circular layer of adhesive foil. Circular DSCD's conveniently measuring 4 cm in diameter are cut around the tape-encased activated charcoal gel. The DSCD is then placed in a suitable cleansed (defatted with soap or isopropyl alcohol) hairless part of the body (e.g., back or ankle) or is stored for later use.

During use or after the DSCD is removed from the body, the chemical of interest which has migrated into the DSCD and accumulated on the binding reservoir must be detected or measured in order to interpret body content during the period of monitoring. This may be accomplished by incorporation of a direct-reading chemical, immunochemical or electro-chemical detection system directly in conjunction with the DSCD or the DSCD may be disassembled for further analytic processing of the reservoir-bound chemical. As an example of the latter, consider a water/agarose gel/activated charcoal DSCD devised to monitor exposure to parathion. After wearing the DSCD throughout a period of exposure (1 hour to 1 week), the gel/activated charcoal matrix is separated from the removed DSCD and placed in 0.5 ml of concentrated HCl which dissolves the gel. The liquid phase of the mixture which contains some parathion resulting from the action of the acid on the activated charcoal is then separated from the charcoal by centrifugation and is saved. The charcoal is subjected to extraction by tumbling it in 1 ml of toluene for 30 minutes; following centrifugation and saving the liquid phase, the sides of the test tube are washed downwards using 0.5 ml of methanol. This procedure is repeated once and all saved liquid phases are combined and brought to dryness by nitrogen evaporation. Greater than 90% of charcoal-bound parathion can be separated using this procedure. The dried residue is then reconstituted in 0.5 ml of mobile phase for high pressure liquid chromatography analysis (HPLC). Using the following HPLC conditions, total parathion separated from the charcoal can be detected and quantitated: Column-Bondapak C18 by Waters Associates, 1.0 ml/min. flow rate, MeOH/$H_2O$/glacial acetic acid in proportion 70/29/1, U. V. determined at 280 nm.

The following disclosure describes the fabrication of a preferred embodiment of the dermal substance collection device according to this invention as depicted in the drawing of FIG. 4.

Initially a layer of 3M brand one-sided adhesive tape (white opaque strippable layer on transparent double sided adhesive layer) is applied to the strippable backing layer side of 3M brand closed-cell foam polyurethane adhesive tape and a hole of dimension about 0.9 cm is created in the compound laminate.

The resulting compound laminate with orifice is applied to a layer of plastic, for example, a sheet of polyvinylidene plastic such as Sara Wrap brand to create a plastic-polyurethane foal interface. The white opaque topside layer of the first compound laminate is then stripped exposing an adhesive surface. A second closed-cell foam polyurethane layer having a larger hold (about 1.2 cm) than the first compound laminate is placed on the exposed adhesive layer of the first laminate with the axes of the hole cylinders aligned so as to create a well mold with a larger upper diameter relative to the smaller lower diameter having the polyvinylidene plastic bottom.

A selected immobilized liquid gel component such as saline agarose with dispersed activated charcoal is poured hot into the created mold and allowed to cool and gel resulting in, from a side view according to FIG. 4, the preferred "mushroom" shaped positive pressure contact gel of this invention upon stripping of the narrower diameter foam layer with the polyvinylidene backing. The bottom stem portion 4 can have a variable 0.5 mm to about 7 cm diameter ranging conveniently, preferably from about 3 cm in order to insure sufficient surface area for dermal contact. Subsequent to formation of the selected gel, the uppermost strippable backing (on opposite side of the laminate remote from the polyvinylidene layer) is removed leaving exposed a surface of closed-cell polyurethane foam to which is applied an occlusive covering of foil such as flesh colored aluminum foil supplied by 3M, the bonding of which is facilitated by interlaid transparent double sided adhesive.

In use, the "bottom" narrower diameter foam layer with plastic backing is stripped exposing a stub or raised cylinder of gel to promote positive pressure contact with the skin; the "upper" bulk of the gel is surrounded by the remaining foam layer with adhesive lower surface for retention on the dermal surface to which applied. The whole device when applied to a dermal surface may be further held in place and protected from unintentional removal by an additional adhesive overlying layer such at "The Pink Tape", a plastic zinc oxide-containing adhesive tape by Nu-Hope Laboratories described as washable, flexible and waterproof.

The optimal device structure consists of a generally flat (1 mm to 0.5 cm thick, preferably 1-2 mm), circular (about 1 to 5 cm, preferably 1 to 3 cm diameter disk) gel matrix containing the binding reservoir which is occluded against skin by larger occlusive aluminum foil and adhesive circles having an adhesive surface sufficient for binding. A device found useful is about 1-2 mm thick, has a 1.5 cm diameter disk, a 2 cm diameter foil and 4 cm diameter adhesive cover.

In addition to the inventive embodiment described in detail above, a number of additional component systems are considered useful within the broad scope of this invention. It will be apparent that in some instances the binding reservoir can also serve the dual function of an immobilizing agent generating, for example, a gel or a paste with the liquid medium dependent on its chemical and/or physical properties such as particle size in the colloid range.

In addition to activated charcoal, molecular sieves, silica gels, modified with aromatic or aliphatic group-containing silanes, various activated alumina, ion exchange resins and chelating agents such as ethylenediaminetetraacetic acid are examples of binding reservoirs. Molecular sieves are alkaline metaloaluminosilicates quite similar to many natural clays and feldspars. When the water of hydration is driven off, the crystal does not collapse or rearrange as is the case for most other hydrated metals. Instead, the physical structure of the crystal remains unchanged which results in a network of empty pores and cavities that comprise about one-half of the total volume of the crystals. Molecular sieves generally have a total (internal and external) potential surface area of 650 to 800 square meters per gram, while the external surface area is only one to two square meters per gram. Due to their unique crystalline structure, molecular sieves have cavities and pores of uniform size. This uniformity permits a sieving or screening action in the molecular size range making separation easy and specific. The material is supplied in powder and pellet forms. These materials are considered valuable in trapping alcohol.

Silica-gel is considered useful to trap highly polar liquids. In a given homologous series such as ethyl alcohol, propyl alcohol, and butyl alcohol, the extent of absorbability decreases in order of decreasing polarity. Compounds with hydroxyl groups such as alcohols and phenols are strongly absorbed as well as oxygen-containing compounds such as esters, aldehydes, ketones, and organic acids. The selectivity of the particular grade of silica gel to determine the preferential absorption of one compound over another depends upon the pore diameter and partially upon the mesh size and percolation rate. In the case of digoxin, incorporation into the subject collection device of the digoxin binding resin, cholestyramine, is considered useful. Digoxin, bound to the strongly basic cholestyramine resin, can be released by mixing in strong alkali.

The liquid medium when aqueous should contain an osmotically active substance such as sodium chloride or albumin; amounts up to and including saturation amounts are acceptable. An aqueous saline solution optimally containing about 30% (30 g salt/100 g water) salt sodium chloride has been found preferable.

For some chemical substance to be collected, it may be desirable to provide with the liquid medium a penetration enhancing amount, for example, 0.01% upward to 20% by weight of the liquid medium, of a penetration enhancing agent which can be glycerine or preferably one or a mixture of n,n-diethyl-m-toluamide, 1-dodecylazacycloheptan-2-one, or dimethylsulfoxide which may augment the movement of substance into the collection device. In the instance where the liquid medium is immobilized as an aqueous gel, the penetration enhancing agent may be contained on the gel surface which is to be placed in contact with the dermal surface. It has also been found advantageous to apply alternatively a small amount of the penetration enhancing agent directly to the skin prior to placement of the collection substance of the device on the agent. The binding reservoir component can be present in an amount from about 0.5% to about 30% by weight of binding agent based on the weight of the liquid transfer medium in which incorporated. Activated charcoal present in saline at about 5% has been found acceptable. The gelling agent is present in a gelling amount. For example, about 0.5% to about 30% agarose has been found acceptable. Agarose in an amount of about 3-4% has been found to be suitable in, for example, a 5% saline system.

In addition to aqueous gels containing the natural gelling agent agarose, gel matrices containing other natural or synthetic gelling agents such as polyvinyl alcohol in gelling amounts are also suitable for use in the device of this invention. Suitable gelling agents can be selected from the polymers or polymeric mixtures disclosed in U.S. Pat. No. 4,321,252, the disclosure of which, in this regard, is hereby specifically incorporated by reference.

A prototype gel consists of 4% in 30% saline. Pulverized activated charcoal mixed into the gel @5% by weight serves as a suitable binding reservoir and provides quantitative binding for weak aqueous solutions of theophylline, delta-9-tetrahydrocannabinol, parathion, dimethylacetamide, cimetidine and nicotine. The following binding reservoir materials (with the chemical to be bound in parentheses) are useful in this invention: Whatman PSI ion exchange paper (na, Li, Pb); Na polystyrene sulfate Kayexalate brant (Na,Li); gel and paper bound antibodies (theophylline); activated charcoal cloth (theophylline); Amberlite IR 120+2 (Na); Dowet HGR—H HCR—S—H (Na).

Examples of additional procedures for off-loading bound chemical from gel/charcoal disks which have been developed are as follows (with the solvent system in parentheses): theophylline (Acid/toluene/methanol), parathion (acid/tolune/methanol), delta-9-tetrahydrocannabinol (toluene/ethanol), and nicotine (acid/methanol/ethanol). Non-acid gel disruption techniques including the use of sonication, heat, DMSO, KI, and Na perchlorate, and an off-loading procedure for theophylline bound to antibody paper are also applicable to this invention.

For study of the broad utility of this invention, selected model chemicals of the group theophylline, delta-9-tetrahydrocannabinol, parathion, dimethylacetamide, cimetidine, nicotine, inulin, T-2 mycotoxin were chosen in part because together they exhibit physicochemical properties which span broad ranges of molecular size, water/fat solubility and acid/base dissociation properties.

Extensive In vivo testing of the dermal substance collection device (DSCD) has been undertaken in rabbits (R, Rhesus monkeys (M) and humans (H). Orally or intravenously administered substances for dermal collection have included aminophylline 80% theophylline, or 20% ethylenediamine (R,M), 14C-nicotine (M), 22-Na (R), 14C-parathion (R,M), delta-9-tetrahydrocannabinol THC (M,H), 14C-inuline (M), cimetidine (M,H), and dimethylacetamide (M). Experimental conditions were varied in order to evaluate various binding reservoirs including activated charcoal dispersed in a saline/gel matrix, various DSCD embodiments which provide a liquid bridge including saline, immobilized by various gels such as agarose or polyvinyl alcohol as the gelling agent, various DSCD embodiments which provide persistent occlusive contact of the liquid bridge with the skin (single layer adhesive tape overlying the DSCD liquid bridge/binding reservoir complex vs multiple tape/foil layers enveloping a liquid bridge/binding reservoir complex vs multiple tape/foil layers enveloping a liquid bridge/binding reservoir complex which protrudes into the skin effecting positive pressure during emplacement), various preparatory procedures (shaving, clipping of hair, use of a chemical depilatant, cleansing of the skin with soap and isopropyl alcohol), and various skin penetration enhancing agents (Azone, DET, DMSO).

Figure 6:
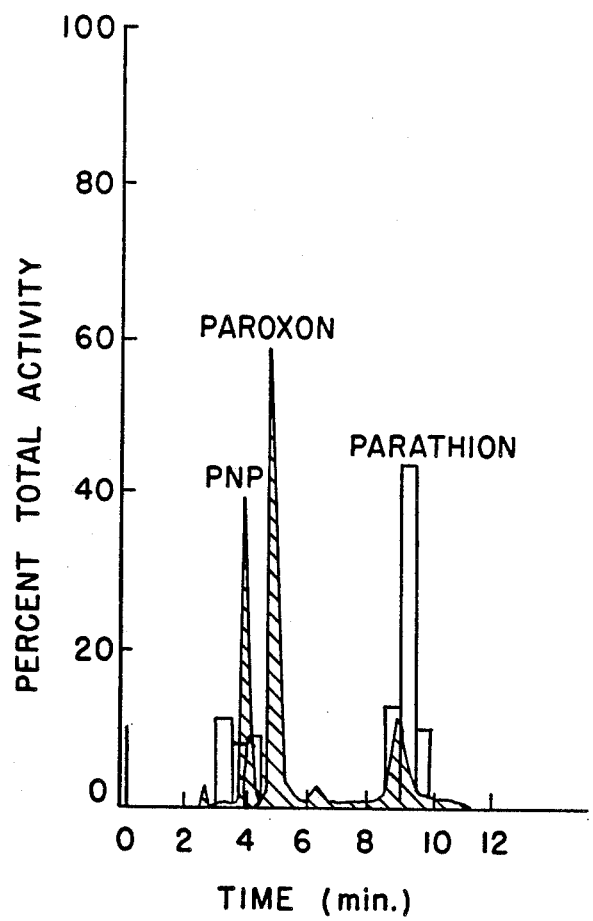
FIGS. 6 and 7 graphically depict experimental results involving use of a device according to the present invention to monitor a radiolabeled chemical.
Figure 7:
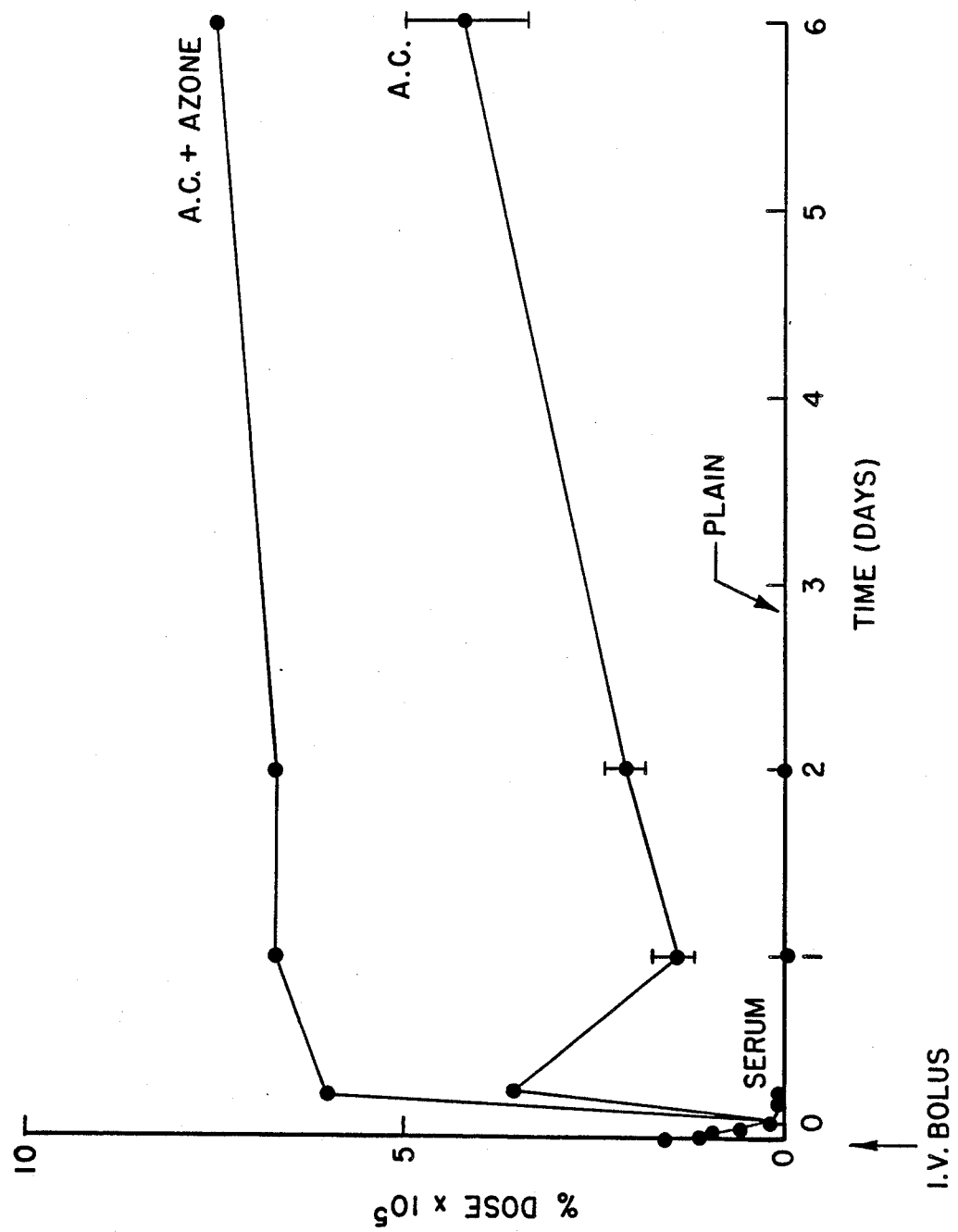

In a typical animal experiment, a Rhesus monkey is anesthetized with ketamine 10 mg/kg and the hair on the chest and abdomen is clipped prior to washing the underlying skin (with a mild soap or isopropyl alcohol). Up to 30 DSCD's are emplaced on the skin after which a non-toxic dose of non-radioactive test-substance or 50 uCi of 14C-labeled test-substance is injected intravenously into a leg vein. Blood samples are taken at intervals ranging from 20 minutes to 96 hours; DSCD's are removed at intervals ranging from 3 hours to 96 hours. Blood plasma samples are analyzed for the test-substance and its known metabolites (1) in a non-radioactive experiment by an appropriate chemical assay (e.g. high pressure liquid chromatography [HPLC], gas chromatography [GC], radio-immunoassay [RIA], enzyme-immunoassay [EI], etc.); (2) in a radioactive experiment by scintillation counting techniques applied to the plasma directly or following chromatographic separation of derivatives of the test-substance. The binding reservoir elements of the DSCD's are subjected to chemical extraction of the charcoal-bound test-substance derivatives using organic solvent extractants in conjunction with disruption of the gel/binding reservoir or vigorous tumbling or sonication. The extracted test-substance derivatives may be further subjected to chromatographic separation followed by direct chemical detection (non-radiolabeled test-substances) or scintillation counting (radio-labeled test-substance). FIGS. 6 and 7 depict results of a typical animal experiment involving 14C-parathion as the test substance.

FIG. 6 describes the chromatographic separation of extracted transepidermal liquid collected at 24 hours on a rhesus monkey (open bars). The percent activity of the eluant collected every 30 seconds (0.5 ml) following extraction and chromatographic separation of DSCD device liquid is plotted as a function of time. The hatched areas represent the chromatogram obtained for parathion, paroxon, and p-nitrophenol (pnp) standards. Chromatographic conditions are substantially the same as those described previously.

FIG. 7 shows the time course of transdermal dosimetry of 14C-parathion injected intravenously in a rhesus monkey. The device contained agarose gel without ("pain") or with dispersed activated charcoal (A.C.), the underlying skin being untreated or pre-treated with Azone. A.C. gel DSCD devices using Azone showed particularly satisfactory transdermal collection.

TABLE 1

EXTENT OF SUBSTANCE COLLECTION IN ANIMAL STUDIES EMPLOYING AGAROSE GEL/ACTIVATED CHARCOAL DSCS'S

| TEST-SUBSTANCE | EXTENT OF TRANSDERMAL MIGRATION* (% Dose × $10^4$) |
|---|---|
| THEOPHYLLINE | 25 |
| NICOTINE | 2.5 |
| PARATHION | 0.7 |
| TETRAHYDROCANNABINOL | 0.1 |
| INULIN | 0.5 |
| CIMETIDINE | 8.3 |
| DIMETHYLACETAMIDE | 8.4 |

*These values represent collection of all test-substance relative derivatives (includes parent compound and metabolites) except in the cases of THC and cimetidine which reflect the collection of parent compound only. The diameter of the liquid bridge contact with the skin was 9 mm.

Table 1 summarizes the results of studies in Rhesus monkeys of the above-named test substances in terms of the maximum percentage of the administered dose collected in agarose/activated charcoal DSCD's.

Preliminary studies using the DSCD's have been undertaken in humans ingesting either delta-9-tetrahydrocannabinol (THC) or cimetidine. Eighteen DSCD's (1 cm gel diameter) were emplaced for up to 48 hours on the lower legs of a cancer patient after receiving orally a single gelatin capsule containing 10 mg THC. Assaying the THC by RIA following extraction of the gel/activated charcoal complex with toluene/ethanol yielded 224 +/−22 pg of THC from DSCD's containing agarose gel without activated charcoal and 601 +/−302 pg THC from DSCD's containing gel with activated charcoal. In one healthy human volunteer, twelve DSCD's each (25 mm liquid bridge diameter, all containing agarose gel and activated charcoal) emplaced for 24 hours on posterior-aricular, ventral forearm and medical lower leg areas after receiving orally or intravenously 5 mg/kg cimetidine solution or tablets yielded 62–461 ng cimetidine (assayed by HPCC).

Variations of the embodiments of this invention as disclosed above will be apparent to the skilled artisan having the benefit of this disclosure. These modifications are to be considered within the scope of the claims to this invention which follow.

The DSCD according to this invention may be viewed as having broad utility for monitoring cumulative exposure of mammals including man to chemicals.

I claim:

1. A method for the non-invasive, immediate and continuous collection of a chemical substance from a dermal surface, said method comprising the steps of
I. applying to the skin to collect said chemical substance from said surface a dermal surface a dermal substance collection device (DSCD) comprised of:
  (a) a binding reservoir material for binding with said dermal substance to prevent back transfer loss of said dermal substance from said collection device to the dermal surfaces;
  (b) a liquid bridge transfer medium which allows the instantaneous and continuous transfer of said dermal substance from the dermal surface to said binding reservoir material, said binding reservoir material being maintained in a wet-state by said liquid bridge transfer medium; and
  (c) a cover means for occlusively containing said binding reservoir material and said liquid bridge transfer medium and for occlusively maintaining said liquid bridge transfer medium in continuous contact with the dermal surface upon application of said collection device to the dermal surface;
II. maintaining the DSCD in a substantially air tight relation with the skin surface over the collection period;
III. removing the binding reservoir material from the DSCD; and
IV. analyzing the chemical substance collected in the binding reservoir.

2. A method according to claim 1 wherein the dermal substance collection device has a circular shape and a substantially flat profile relative to the dermal surface upon adhesive application thereto.

3. A method according to claim 1 wherein the dermal substance collection device has an immobilized liquid transfer medium approximately 1 millimeter to 7 centimeters in diameter and 1 millimeter to 0.5 centimeters in thickness.

4. A method according to claim 1 wherein the dermal substance collection device has a strippable backing.

5. A method according to claim 1 wherein said liquid bridge transfer medium is immobilized.

6. A method according to claim 5 wherein said binding reservoir is selected from the group consisting of activated charcoal, ion-exchange resin, immobilized antibody, silica, zeolite and molecular sieve.

7. A method according to claim 5 wherein said occlusive cover means is comprised of an outer adhesive layer and an inner metallic foil layer contiguous to said immobilized liquid bridge transfer medium.

8. A method according to claim 18 wherein said occlusive cover means further comprises a transfer medium-surrounding closed-cell foam layer contiguous to said foil layer.

9. A method according to claim 5 wherein said immobilized liquid bridge transfer medium comprises a protruding surface relative to the occlusive cover means and the dermal surface-interface to maintain positive pressure contact between said transfer medium and said dermal surface.

10. A method according to claim 5 wherein said binding reservoir material is dispersed in said immobilized liquid bridge transfer medium.

11. A method according to claim 10 wherein said binding reservoir material is activated charcoal and said immobilized liquid bridge transfer medium is an aqueous gel.

12. A method according to claim 11 wherein said aqueous gel comprises an osmotically active substance.

13. A method according to claim 12 wherein said aqueous gel consists essentially of an osmotically active aqueous solution and an agarose gelling agent.

14. A method according to claim 13 wherein said osmotically active aqueous solution contains sodium chloride present in an amount up to saturation of said aqueous gel.

15. A method according to claim 14 wherein the amount of agarose is 0.5 to 30% by weight of the aqueous sodium chloride solution and the amount of activated charcoal is 0.5 to 30% by weight of the aqueous gel.

16. A method according to claim 15 wherein the amount of agarose is about 3 weight-percent of the sodium chloride solution and the amount of activated charcoal is about 5 weight-percent of the aqueous gel.

17. A method according to claim 11 wherein said aqueous gel comprises an agarose gelling agent.

18. A method according to claim 11 wherein said aqueous gel comprises a polyvinyl alcohol polymer gelling agent.

19. A method according to claim 18 wherein the penetration enhancing agent is selected from the group consisting of n,n-diethyl-m-toluamide, 1-dodecylazacycloheptane-2-one, and dimethyl sulfoxide.

20. A method according to claim 7 wherein said aqueous gel comprises a penetration enhancing agent.

* * * * *